United States Patent
O'Donnell et al.

(10) Patent No.: US 12,357,359 B2
(45) Date of Patent: Jul. 15, 2025

(54) BONE REDUCTION AND FIXATION PLATE

(71) Applicant: ARC TECHTONICS, INC., Hampton, NH (US)

(72) Inventors: Turlough O'Donnell, Dublin (IE); Alan Laing, Dublin (IE)

(73) Assignee: Arc Techtonics, Inc., Hampton, NH (US)

( * ) Notice: Subject to any disclaimer, the term of this patent is extended or adjusted under 35 U.S.C. 154(b) by 0 days.

(21) Appl. No.: 18/596,579

(22) Filed: Mar. 5, 2024

(65) Prior Publication Data

US 2024/0206930 A1    Jun. 27, 2024

Related U.S. Application Data

(63) Continuation of application No. 17/601,507, filed as application No. PCT/EP2020/059817 on Apr. 6, 2020, now Pat. No. 12,070,254.

(30) Foreign Application Priority Data

Apr. 5, 2019 (GB) ...................................... 1904862

(51) Int. Cl.
*A61B 17/80* (2006.01)

(52) U.S. Cl.
CPC ...... *A61B 17/8076* (2013.01); *A61B 17/8014* (2013.01)

(58) Field of Classification Search
CPC ........................ A61B 17/8061; A61B 17/8076
See application file for complete search history.

(56) References Cited

U.S. PATENT DOCUMENTS

| | | |
|---|---|---|
| 7,635,365 B2 | 12/2009 | Ellis et al. |
| 8,906,070 B2 | 12/2014 | Medoff |
| 8,911,482 B2 | 12/2014 | Lee et al. |
| 8,998,904 B2 | 4/2015 | Zeetser et al. |
| 9,283,008 B2 | 3/2016 | Gonzalez-Hernandez |
| 9,333,014 B2 | 5/2016 | Gonzalez-Hernandez |
| 9,421,103 B2 | 8/2016 | Jeng et al. |
| 9,775,657 B2 | 10/2017 | Bernstein et al. |
| 9,877,754 B2 | 1/2018 | Patel et al. |
| 10,182,845 B2 | 1/2019 | Grant |

(Continued)

FOREIGN PATENT DOCUMENTS

| | | |
|---|---|---|
| CN | 201234999 Y | 5/2009 |
| CN | 202027696 U | 11/2011 |

(Continued)

OTHER PUBLICATIONS

International Search Report and Written Opinion for PCT Patent Application No. PCT/EP2020/059817, mailed Sep. 11, 2020, 14 pages.

(Continued)

*Primary Examiner* — Olivia C Chang
(74) *Attorney, Agent, or Firm* — Adler Pollock & Sheehan P.C.

(57) ABSTRACT

A bone reduction and fixation device (1, 70) comprises an elongated biplanar plate along most of its length having an L-shaped profile defined by a first plate surface (3A, 4A) and one or more second plates (3B, 4B), in which the first and second plates comprise a plurality of countersunk holes (8) configured for receipt of bone-fixing screws (10).

10 Claims, 14 Drawing Sheets

(56) References Cited

U.S. PATENT DOCUMENTS

| | | | |
|---|---|---|---|
| 10,631,902 | B2 | 4/2020 | Weiner et al. |
| 11,141,205 | B2 | 10/2021 | Cox |
| 2005/0171544 | A1 | 8/2005 | Falkner |
| 2007/0185493 | A1 | 8/2007 | Feibel et al. |
| 2008/0082101 | A1* | 4/2008 | Reisberg ............ A61B 17/8076 606/151 |
| 2009/0210010 | A1 | 8/2009 | Strnad et al. |
| 2009/0306724 | A1 | 12/2009 | Leither et al. |
| 2009/0312759 | A1 | 12/2009 | Ducharme et al. |
| 2010/0198266 | A1 | 8/2010 | Nassab |
| 2010/0217328 | A1 | 8/2010 | Terrill et al. |
| 2010/0256687 | A1 | 10/2010 | Neufeld et al. |
| 2014/0172020 | A1 | 6/2014 | Gonzalez-Hernandez |
| 2014/0180344 | A1 | 6/2014 | Gonzalez-Hernandez |
| 2014/0277176 | A1 | 9/2014 | Buchanan et al. |
| 2015/0209093 | A1 | 7/2015 | Dallis |
| 2015/0245858 | A1* | 9/2015 | Weiner ............... A61B 17/8061 606/280 |
| 2019/0059965 | A1 | 2/2019 | Gausepohl et al. |
| 2019/0183549 | A1 | 6/2019 | Singh |

FOREIGN PATENT DOCUMENTS

| | | |
|---|---|---|
| CN | 107320169 A | 11/2017 |
| CN | 207084848 U | 3/2018 |
| CN | 207561971 U | 7/2018 |
| CN | 108904031 A | 11/2018 |
| CN | 108926380 A | 12/2018 |
| CN | 208481441 U | 2/2019 |
| CN | 208784886 U | 4/2019 |
| CN | 109907810 A | 6/2019 |
| CN | 209136840 U | 7/2019 |
| CN | 209611280 U | 11/2019 |
| CN | 209884296 U | 1/2020 |
| CN | 209932949 U | 1/2020 |
| CN | 212816484 U | 3/2021 |
| CN | 212816485 U | 3/2021 |
| CN | 213075872 U | 4/2021 |
| FR | 3003749 A1 | 10/2014 |
| GB | 2435429 B | 3/2008 |
| JP | S5883954 A | 5/1983 |
| JP | 2011019710 A | 2/2011 |
| JP | 2012518467 A | 8/2012 |
| JP | 5728615 B1 | 6/2015 |
| JP | 2016104061 A | 6/2016 |
| WO | 2017207922 A1 | 12/2017 |
| WO | 2019126319 A1 | 6/2019 |
| WO | 2021175724 | 9/2021 |
| WO | 2022086455 A1 | 4/2022 |

OTHER PUBLICATIONS

International Search Report and Written Opinion for PCT Patent Application No. PCT/US2022/077606, mailed Jan. 13, 2023, 14 pages.

Office Action for GB Patent Application No. 2114235.1, mailed on Feb. 10, 2022, 4 pages.

Office Action for Japanese Patent Application No. 2021-560439, mailed on Dec. 26, 2023, 12 pages (6 pages of English Translation and 6 pages of Official Copy).

Acumed, "Clavicle Plating System," Product Brochure Jul. 2021, 16 pages, downloaded from https://www.acumed.net/wp-content/uploads/2021/07/Acumed-EN-Clavicle-Plating-System-Brochure-SHD00-04-B.pdf.

Joeris, et al., "The impact of the AO Foundation on Fracture Care: An Evaluation of 60 years AO Foundation," Injury, Int. J. Care 50 (2019) 1868-1875.

Kitzen, et al., "Biomechanical Evaluation of Different Plate Configurations for Midshaft Clavicle Fracture Fixation: Single Plating Compared with Dual Mini-Fragment Plating," JBJS Open Access, 2022:e21.00123.

Uhthoff, et al., "Internal Plate Fixation of Fractures: Short History and Recent Developments," J Ortho Sci (2006) 11:118-126.

* cited by examiner

BONE REDUCTION AND FIXATION PLATE

CROSS REFERENCE TO RELATED APPLICATIONS

This application is a continuation of U.S. application Ser. No. 17/601,507, filed Oct. 5, 2021, which is a national phase filing under 35 U.S.C. § 371 of International Application PCT/EP2020/059817, filed Apr. 6, 2020, which claims benefit of priority to United Kingdom Patent Application No. 1904862.8, filed Apr. 5, 2019, the entire contents of which are hereby incorporated by reference herein.

FIELD OF THE INVENTION

The present invention relates to a plate for fixation of fractures. Also contemplated are methods of reduction and fixing of bone fractures, especially clavicular fractures.

BACKGROUND TO THE INVENTION

The clavicle or collarbone is a long bone that serves as a strut between the shoulder blade and the sternum. Humans have two clavicles, left and right. It is the most commonly fractured bone in the body, accounting for 5% of all bone fractures. Approximately 17,000 clavicle fractures are reported daily on a global basis. The clavicle can be fractured due to direct impact on the bone, or due to impact to the shoulder from the force of falling on outstretched arm. When viewed from the front (anterior view), the bone has a generally straight appearance, and when viewed from above (superior view) it has a two-curve configuration from the sternal end to the acromial end, a so-called "lazy S" shape. About 5% of clavicle fractures occur at the sternal end (medial fractures), 10-15% occur at the acromial end (lateral fractures), and the vast majority of fractures occur in the midshaft (80-85%). Treatment of clavicle fractures include conservative treatments (treatment without surgery). This is a successful treatment for undisplaced 2-part clavicle fractures. However, if the fracture is significantly displaced or comminuted (in more than 2 pieces), conservative treatment results in a higher incidence of non-union or malunion of the fracture, which can cause significant persistent weakness and disability even if the fracture heals. It is generally accepted that surgical treatment of fractures is indicated for comminuted fractures, widely displaced and shortened fractures, segmental fractures and "Z-type" fractures. The most common surgical treatment for serious clavicle fractures involves use of superior plate fixation or anteroinferior plate fixation. These are monoplanar plates having a series of holes for receipt of bone fixation screws. In order to have the required strength to resist torsional and bending stiffness, these plates have to have a thickness of at least 4 mm along their length, which is quite large for an implant in this area of the skeleton, and uncomfortable for the patient. In addition, it is possible to use a percutaneous intramedullary screw, which has gained some popularity in recent years.

In the case of comminuted fractures, segmental fractures and Z-type fractures, it is extremely difficult to reduce the bone fragments and fix them in place with a plate, and the fragments need to be reduced point-to-point while the fixation wires or screws are fixed in place. The deforming forces of the muscles often prevent the reduction holding in place, and it can be extremely difficult to fix the plate to the bone before the fracture displaces. Superior plate fixation is most commonly utilized because it makes the bone fragment reduction a little easier, but the plates tend to be weak in bending stiffness, and do not allow early mobilization of the shoulder, as there is a significant risk of the plate bending and the fixation failing. In addition, the plate is quite superficial and usually palpable through the skin. It is not uncommon for the patient to request removal of the plate once the fracture has healed.

Anteroinferior plate fixation provides better bending stiffness, as it increases the area moment of inertia, but it is extremely technically difficult to accurately reduce clavicle bone fractures using anterior plates. In addition, it is impossible to reduce the comminuted fragments once the plate has been applied. Anteroinferior plates also contribute to devascularisation of the bone at the fracture site. Intramedullary screw or pin fixation is also technically challenging, and it is particularly difficult to reduce the fracture. It is unsatisfactory in fixing comminuted fragments, as it does not provide adequate stability at the fracture site. Indeed, due to the difficulty of both superior and anteroinferior plate fixation, as well as intramedullary screw fixation, many orthopaedic surgeons elect a conservative, non-surgical treatment, which commonly lead to non-union or malunion. This has a detrimental effect on long-term shoulder girdle function.

Bone fixation and reduction plates are described in WO2019/126319, FR3003749, JP2016-104061, CN108904031, and CN108926380.

It is an object of the invention to overcome at least one of the above-referenced problems.

SUMMARY OF THE INVENTION

The present invention addresses the need for a bone fracture reduction plate that facilitates reduction and fixing of bone fragments in a patient with a bone fracture, including a comminuted clavicular fracture, elbow (olecranon) fractures, and ankle (fibula) fractures. The device is an elongated contoured biplanar plate formed by two or more surfaces orientated at approximately 90° to each other. Most or all of the device has an L-shaped profile that facilitates aligning bone fragments with the plate, allowing for easier and guided bone reduction, and allowing fixing screws to be introduced into the bone at right angles to each other.

The L shaped profile of the plate allows the plate to be thinner along most, substantially all, or all of its surface, for example about 2-3 mm (which is more comfortable for the patient), while allowing for greater bending and torsional stiffness (which allows for early and aggressive mobilisation of the shoulder), as the area moment of inertia is increased in both the coronal and axial planes. The plates typically comprise countersunk holes (although can also accommodate traditional headed screws) for receipt of fixing screws, which are generally configured so that the heads of the screws do not extend proud of the surface of the plates, and generally are flush with the plate surface. There will be the option of locking or non-locking screws.

In one embodiment (which is especially suited for reduction and fixing of clavicle fractures), the central section of the plate is uniplanar (i.e. not L shaped). This provides a "lag window" to allow comminuted fragments of bone to be fixed in place, typically via a lag screw technique, at the point of fracture. This will generally be achieved once the initial step of anatomical reduction has been achieved via the technique of reduction. It also allows for the healing bone fragments to be adequately vascularised, by avoiding devascularisation of the healing fragments due to compression on the microvasculature by the plate. This should theoretically improve the quality and rate of healing and hence return to function.

In embodiments where the central section does not have the strong L-shaped profile, the Applicant has discovered that this is an obvious point of weakness and potential failure, so the section of the surface forming the central part of the device will generally have an increased thickness, for example 4.5 mm, than the medial and lateral sections of the first plate for the length of the "lag window" to maintain bending and torsional stiffness. In one embodiment, to avoid stress concentrations on the plate, the increase in thickness of the first surface should be sloped and smooth, and not sharp and abrupt (in other words a gradient).

In use with a clavicle fracture, the plate should generally initially be fixed to the medial, or sternal-end fragment using either wires through 2 mm anteriorly-placed wire holes, or through screw fixation through an anterior oval shaped hole with a traditional/countersunk screw. Using a specialized custom-shaped holding clamp, the medial fragment is reduced onto the lateral, or acromial-end fragment, and the shape of the plate aids in the "capturing" of the lateral fragment. The superior surface then prevents the deforming vertical vector forces from displacing the lateral fragment while initial fixation can be achieved in the lateral fragment by wires or a countersunk screw into an oval fixation hole on the superior surface.

The combination of the anterior medially-based screw and superior laterally-based screw allows for manipulation of the fracture fragments into an anatomically reduced position by the slight loosening of fixation of these screws, allowing the bone fragments to "slide" on the plate up to approximately 5 mm on each side achieving anatomical reduction. Once this has been achieved, fixation of the plate to the clavicle can proceed with a plurality of screws both anteriorly and superiorly. Fixation of the plate with screws at 90° to each other increases the load to failure of the plate.

According to a first aspect of the present invention, there is provided a bone reduction and fixation device comprising an elongated biplanar plate having an L-shaped profile defined by a first plate and one or more second plates.

In one embodiment, the first and second plates comprise a plurality of countersunk holes configured for receipt of bone-fixing screws.

In one embodiment, the device has an L-shaped profile along at least 60% or 70% of its length.

In one embodiment, the plates (or most of the plates) of the biplanar plate have a thickness of less than 3 mm or 2.5 mm. In one embodiment, at least 70% or 80% of the biplanar plate has a thickness of less than 2.5 mm. In one embodiment, at least 70% or 80% of the biplanar plate has a thickness of about 1.5 to 2.5 mm. In one embodiment, the first and second plates in the biplanar regions of the device have a thickness of less than 3 mm or 2.5 mm, for example 1-3 mm, or 1.5-2.5 mm, or about 2 mm.

In one embodiment, the biplanar plate has an L-shaped profile along most or all of its length. This embodiment, is suitable for use in reduction and fixing fractured fibula or olecranon. Generally, in these embodiments, one or both of the first and second plates comprises an elongated slot (12).

In one embodiment, the first plate is connected to the second plate along substantially all of its length (i.e. at least 90%, 95% or 100% of its length). Thus, the join between the plates is continuous or almost continuous along the plate (i.e. the plates are not joined by struts or bars). This provides strength and stiffness to the plate, in comparison to devices of the prior art that include holes or slots along the join region that weaken the plate.

In another embodiment, suitable for reduction and fixing clavicle fractures, the biplanar plate comprises two biplanar L-shaped end sections defined by end parts of the first plate and second end plates, and a monoplanar central section defined by a central part of the first plate, in which the central part of the first plate has a thickness greater than the end parts for example at least 30%, 40% or 50% thicker than the other parts of the biplanar plate. This provides an access window (or "lag window") for the surgeon to access the fracture area and fix comminuted bone fragments via a "lagging" technique. It also provides for less devascularisation of the healing bone fragments.

Typically, the first and second plates in the end sections are joined along substantially all of its length (i.e. at least 90%, 95% or 100% of its length). Thus, the join between the plates is continuous or almost continuous in the L-shaped end section. Typically, the plates are planar.

In any embodiment, the plate is of unitary construction (i.e. a monoblock plate). This means that it is formed as a single plate, and the plate is not made up of a plurality of parts that are assembled after the parts are formed. Typically, the plate is cast in a mould as a single plate.

In any embodiment, the plate is pre-contoured and is configured that the shape of the plate cannot be manipulated after formation due to the torsional stiffness imparted by the biplanar design.

In one embodiment, the second end plates and end parts of the first plate have a thickness of less than 3 mm or 2.5 mm (for example 1.5 to 2.5 mm), and in which the central part of the first plate has a thickness of greater than 3.5 mm, (for example 4-8 mm mm).

In one embodiment, the monoplanar central section extends along about 20% to 40% of the length of the device, typically about 30% to about 40% of the length of the device.

In one embodiment, the first plate and the or each second plate have a width of 5-12 mm.

In one embodiment, the width of the first and/or second plate varies along it length. For example, the width of one or both plates may vary to correspond to conform to the shape of the bone that is being fixed. In the case of the biplanar plate for the fibula, the plates at one end of the device are widened to approximately conform to the end of the fibula.

In one embodiment, the first plate and/or the or each second plate have a width of 5-12 mm.

In one embodiment, the first plate and/or the or each second plate have a width of 8-10 mm.

In one embodiment, the first and second plates each comprise at least 3, 4, 5, 6, 7 or 8 countersunk holes (8).

In one embodiment, the elongated biplanar plate is shaped to approximately correspond to conform a shape of a target bone. For example, with a device for reduction and fixing of a clavicle, the biplanar plate is curved to conform to a curve on an anterior surface of a human clavicle. For example, the second (anterior) plate may be substantially flat and the first (superior or inferior) plate may be curved. In one embodiment, the elongated biplanar plate is pre-contoured and curved to approximately correspond to the shape and curve of the superior (or inferior) surface of a human clavicle.

In any embodiment, the continuous first plate is contoured to match a sigmoid curve on a clavicle bone. In another embodiment, the plate is for reduction of a fracture of the humerous, and one or both plates of the biplanar plate may be contoured to match the curve in the distal part of the humerus.

In one embodiment, at least one of the first and second plates comprises an elongated slot. The slot is configured to allow both lateral and medial movement of the plate with respect to the bone fragments when the screws are slightly loosened.

In one embodiment, the central section of one of the plates comprises an exaggerated elongated slot.

In one embodiment, both of the first and second plates comprise an elongated slot.

In an embodiment of a device for a fractured fibula, the first and second plates may increase in width towards a proximal end of the device to approximately conform to a shape of an end of a human fibula.

In this embodiment, the proximal end of the device may comprise an elongated slot in each plate.

In an embodiment of a device for a fractured olecranon, a heel end of the biplanar plate may be configured to form an end plate dimensioned to abut an end of the olecranon. In this embodiment, the first (sagittal) plate of the heel end of the biplanar plate may comprise a plurality of countersunk holes.

In one embodiment, one or both of the first and second plates include small holes configured to receive fixing wires In one embodiment, the elongated plate is formed from a metal or metal alloy. Suitable metals include stainless steel, titanium, cobalt, and chrome.

In another aspect, the invention provides a use of a bone reduction and fixation device of the invention, for reduction and fixation of a bone fracture. In one embodiment, the bone fracture is a comminuted fracture, in which the device comprises a lag window. In one embodiment, the fracture is a comminuted fracture of the clavicle or olecranon.

In another aspect, the invention provides a use of a bone reduction and fixation device of the invention, for reduction and fixation of a olecranon fracture. In one embodiment, the bone fracture is a fracture of the ulna, in which the biplanar plate comprises an end plate, in which the end plate and anterior plate are dimensioned to conform to the shape of the end of the ulna.

In another aspect, the invention provides a use of a bone reduction and fixation device of the invention, for reduction and fixation of an elbow fracture. In one embodiment, the bone fracture is a fracture of the fibula, in which distal ends of the plates are widened to approximately conform to lateral and posterior surfaces of the fibula.

In another aspect, the invention provides a method of reduction and fixation of a bone fracture (typically a fracture of the clavicle) that employs a bone fracture reduction and fixation plate of the invention, the method comprising the steps of:

aligning the first bone fragment (generally the medial fragment in the case of the clavicle) with a first end section of the plate with the bone fragment typically nestling in the apex of the L-shaped medial section;

fixing the first bone fragment to the first end section of the plate with fixing means (for example wires through 2 mm wire holes, or a screw through a hole or slot)

aligning a second bone fragment (the lateral bone fragment in the case of the clavicle) with a second end section of the plate with the bone fragment typically nestling in the apex of the L-shaped second end section;

adjusting the position of the bone fragments with respect to the plate until the bone fragments are correctly reduced; and fixing the lateral bone fragment to the lateral end section of the plate with fixation means.

In one embodiment, the fixation means is a fixing wire, although fixation screws may be employed for initial fixing. In one embodiment, both end sections of the plate have an oval slot for receiving a fixation screw, anteriorly on the medial section, and superiorly on the lateral section, and the method involves fixation of the first bone fragment (medial) to the medial section of the plate with a screw through the slot, and once the fracture has been initially reduced fixation of the second bone fragment (lateral) to the lateral section of the plate with a screw through the slot, and then at this stage of the procedure loosening the two screws slightly to allow movement of the fragments relative to the plate by movement of the screws along the slots. This allows for fine adjustment of the position of the fragments relative to the plate. This allows for easier and more accurate point-to-point reduction of bone fragments.

In one embodiment, the method includes an additional step of fixing the bone fragments to the plate with fixing screws.

In one embodiment, the bone fracture is a comminuted fracture. In this embodiment, the elongated plate generally has biplanar end sections and a monoplanar central section (i.e. has an access, or "lag" window), and the method includes an additional step of reducing and fixing smaller (comminuted) bone fragments after the plate has been fixed to the medial and lateral bone fragments. Alternatively, the comminuted bone fragments can be fixed to the lateral and medial fragments prior to reduction.

Other aspects and preferred embodiments of the invention are defined and described in the other claims set out below.

BRIEF DESCRIPTION OF THE FIGURES

FIG. 16 is a lateral view of the device attached to the end of a fractured fibula, and FIG. 17 is a posterior view of the device attached to the end of the fractured fibula.

FIG. 18 is a lateral view of the device attached to one end of the fractured olecranon prior to bone reduction, FIG. 19 is a lateral view of the device attached to the fractured ulna after reduction, and FIG. 20 is an anterior view of the device in-situ.

DETAILED DESCRIPTION OF THE INVENTION

Figure 1:
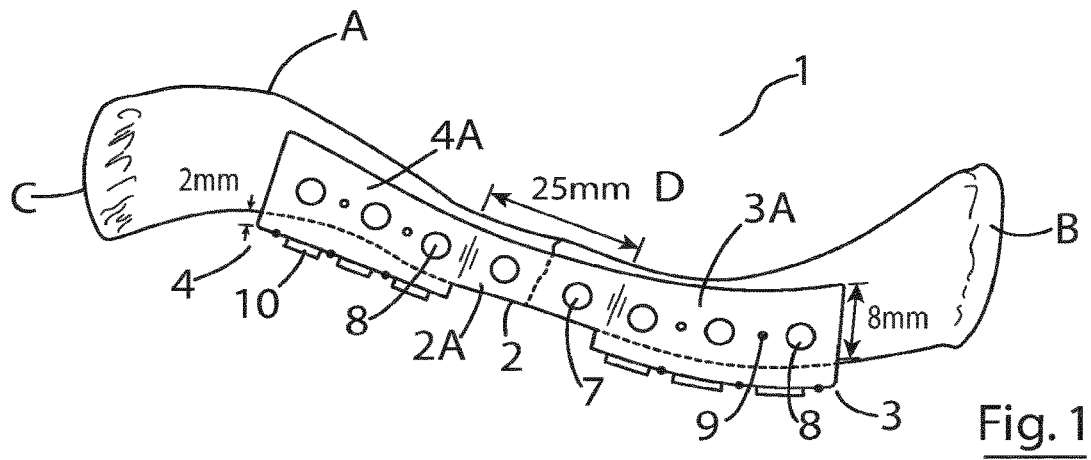
FIG. 1 is an illustration of a bone reduction and fixation plate according to the invention configured for anterior-superior reduction and fixation, shown attached to a fractured right human clavicle (superior view) in an anterior-superior orientation.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human.

As used herein, the term "biplanar" as applied to the device of the invention means that the device has a substantially L-shaped profile along most or all of its length, and generally along at least 60% of its length. Devices of the invention that include a lag window are generally monoplanar along a part of their length (generally along a central section)—these devices are suitable for reduction and fixation of clavicle fractures, especially comminuted clavicle fractures where the lag window allows a surgeon access the smaller fragments of bone and reduce and fix the fragments. Other embodiments of the invention are biplanar along all or substantially all of their length, for examples the devices for reduction and fixing ankle or elbow fractures.

Figure 22A:
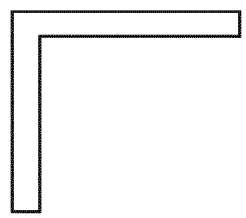
FIG. 22A to 22D are illustrations of the various types of L-shaped profile applicable to the biplanar plate of the invention.
Figure 22B:
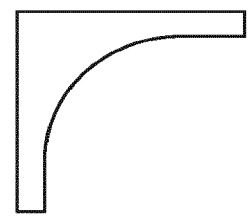
Figure 22C:
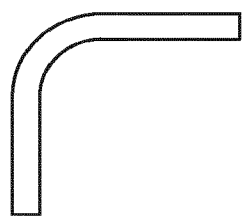
Figure 22D:
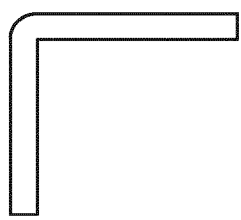

As used herein, the term "L-shaped" profile" as applied to the biplanar plate of the invention means that first plate is orthogonal or nearly orthogonal to the second plate along at least a part of its length, in particular the part of the plate that has holes for receiving bone-fixing screws. This provides structural rigidity and torsional stiffness to the plate, and also allows for fixing screws to be inserted in an orthogonal arrangement. It will be appreciated that the plates do not need to be exactly orthogonal provided that the angle between the plates serves to increase the stiffness of the device compared to monoplanar plates. Examples of L-shaped profiles applicable to the devices of the invention are illustrated in FIG. 22. In any embodiment, a transition zone between plates may be L-shaped (FIG. 22A) or curved (FIG. 22C) to provide a smooth transition from a first plate to an orthogonal second plate. In some embodiments, an inner profile of a plate at a transition zone may be curved and an outer profile at the transition zone may be angular (FIG. 22B). All of these embodiments provide plates that are of increased torsional stiffness compared with monoplanar plates.

As used herein, the term "monoblock" as applied to a plate means that the plate is formed in one piece, generally by casting or moulding. It is distinct from plates that are formed in multiple parts and assembled or contoured after formation.

EXEMPLIFICATION

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIGS. 1 to 4, there is illustrated a bone reduction and fixation device according to the invention suitable for reduction and fixation of a clavicle, and indicated generally by the reference numeral 1. The device 1 has a central section 2, medial end section 3 and lateral end section 4. Each end section 3, 4 has an L shaped profile defined by ends of a first (superior) plate 3A, 4A and two second (anterior) plates 3B, 4B. The central section comprises a central part of the first plate 2A and no second plate, thus providing a lag window 5 which provides a surgeon access to the bone fracture. The first and second plates at the end sections are joined together along the full length of the end section without any gaps in the join. The plate is formed as a pre-contoured monoblock (i.e. cast in one piece).

The plate is formed from stainless steel or titanium, and the second plates (3B and 4B), and end sections of the first plate (4A, 3A), each have a thickness of about 2 mm. The central section of the first plate (2A) has a thickness of about 6 mm, to provide greater bending stiffness at the central (monoplanar) section of the plate. The plate is approximately 100 mm in length, with the central section approximately 30 mm and end sections being each approximately 35 mm. The first and second plates each have a width of about 10 mm.

Figure 4:
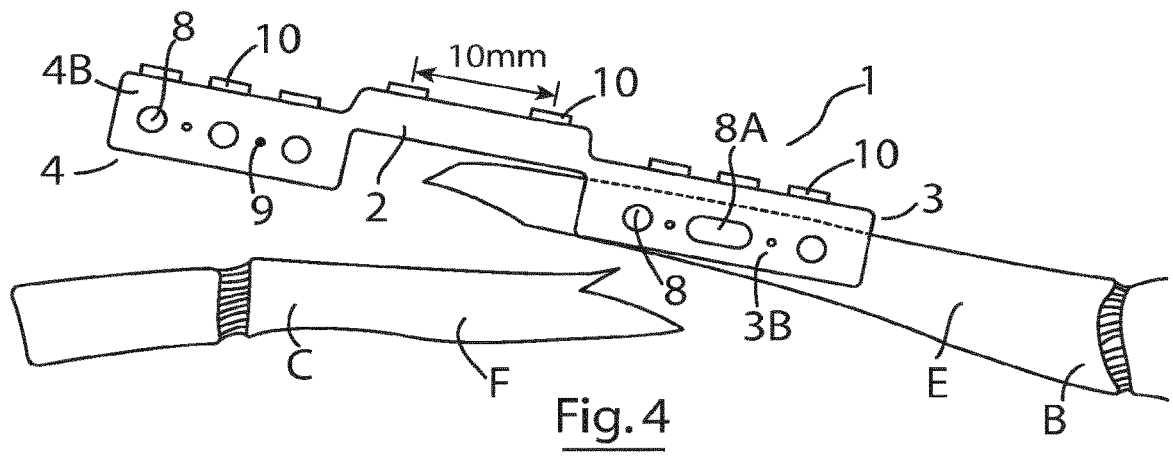
FIG. 4 is an illustration of the bone reduction and fixation plate of FIGS. 1-3 shown attached to the medial bone fragment with the bone nesting in the apex of the L-shaped end section, and prior to alignment of and fixation to the second lateral bone fragment.

The central section 2A of the first plate has two countersunk screw-receiving holes 7, and the end sections of each plate have 3 countersunk screw receiving holes 8. Smaller wire-receiving holes 9 are provided on the plates in between the screw-receiving holes. Screws 10 are shown in the holes in some of the illustrations. In FIG. 4, it can be seen that one of the holes on the second plate 3B has a slightly elongated configuration to form a slot 8A.

Figure 2:
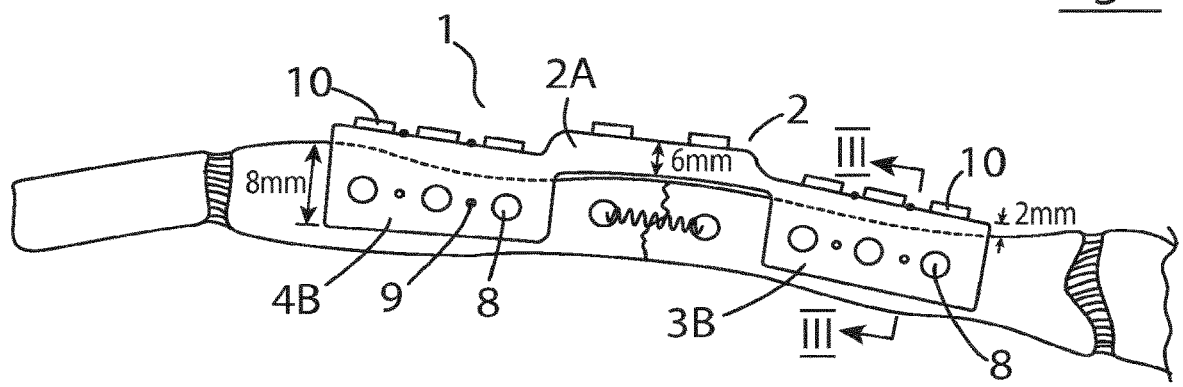
FIG. 2 is an anterior view of the fractured clavicle and bone reduction and fixation plate of FIG. 1.
Figure 3:
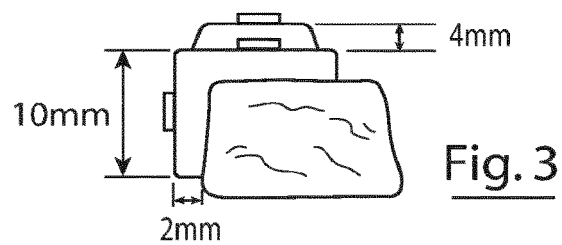
FIG. 3 is a sectional, or sagittal view taken along the lines III-III of FIG. 2.

FIG. 1 is a superior view (from above) showing the device 1 attached to a fractured clavicle A, having a sternal end B and acromial end C, with a break D in the middle section of the bone. The plate 1 is designed to be attached to a clavicle in an superior-anterior orientation (which is best seen in FIG. 1 which is a view from above the clavicle), and has a slight pre-contoured curve along the anterior face which matches the curve on the anterior surface of the clavicle A. FIG. 2 is an anterior view (from the front). FIG. 3 is a cross-sectional sagittal view showing the L-shaped profile of the end sections of the plate, and how a bone fragment (in this case, the medial bone fragment) can nest within the apex of the L-shaped plate allowing easier alignment of the bone with the plate. FIG. 4 is an anterior view of the fractured bone and plate, showing how the medial fragment E can be first attached to the plate prior to attachment of the lateral fragment F.

In use, and referring to FIG. 4, the medial fragment E is aligned with the medial end 3 of the plate, with the bone nestling in the L shaped profile as shown in FIG. 3. Once in position, the bone is fixed to the plate by drilling a hole in the bone through the slot 8A, and inserting a screw into the hole and tightening to fix the medial end of the plate to the medial fragment. The lateral fragment F can then be manipulated to align it with the lateral end 4 of the plate, with the bone nestling in the L-shaped profile of the plate. Once aligned, the lateral position of the fragment F and plate 1 can then be easily adjusted until the fragments of bone reduce together. As the bone fragments both nestle within co-aligned L or C-shaped plates, the only adjustment necessary is lateral adjustment to bring the bones together to reduce. Once they are in position, the lateral fragment F can be fixed to the lateral end section 4 of the plate. At this point, or prior to fixing the lateral fragment of the plate, the position of the medial fragment E with respect to the plate can be fine adjusted by loosening the screw in the slot 8A and slightly adjusting the position of the medial fragment E and plate 1.

Figure 5:
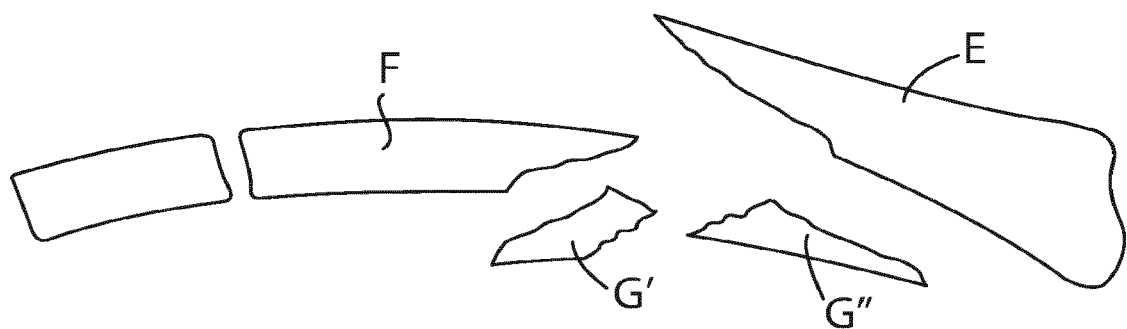
FIG. 5 is an illustration of a typical 4-part comminuted clavicular fracture showing the medial and lateral main bone fragments and two smaller fragments. This is the most commonly seen type of fracture of the clavicle.
Figure 6:
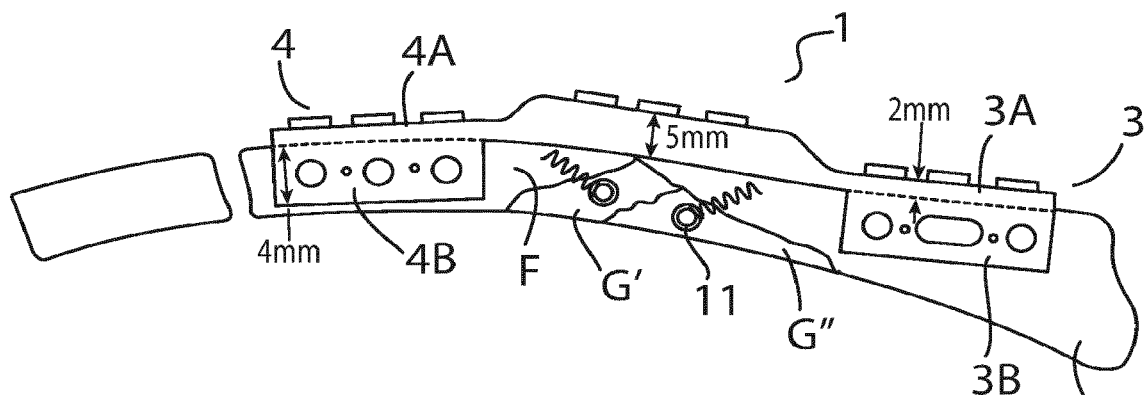
FIG. 6 is an illustration of the plate of the invention attached to the fractured clavicle of FIG. 5, showing how the medial and lateral sections of the plate attach to the main bone fragments, and how the lag window in the central section provides access for the surgeon to the smaller bone fragments allowing them to be reduced and fixed in position.

FIG. 5 shows a comminuted clavicular fracture with a medial bone fragment E, lateral bone fragment F, and comminuted fragments G. The bone reduction and fixing device of FIGS. 1-4 is shown attached to the fractured bone in FIG. 6, with a medial end 3 of the plate 1 attached to the medial fragment E and a lateral end 4 of the plate 1 attached to the lateral fragment F with screws 10. Additional lag screws 11 have been employed to fix the comminuted fragment G' to the end of the lateral fragment F and the comminuted fragment G" to the end of the medial fragment E. The use of this embodiment is substantially the same as that described with reference to FIGS. 1 to 4.

Figure 7:
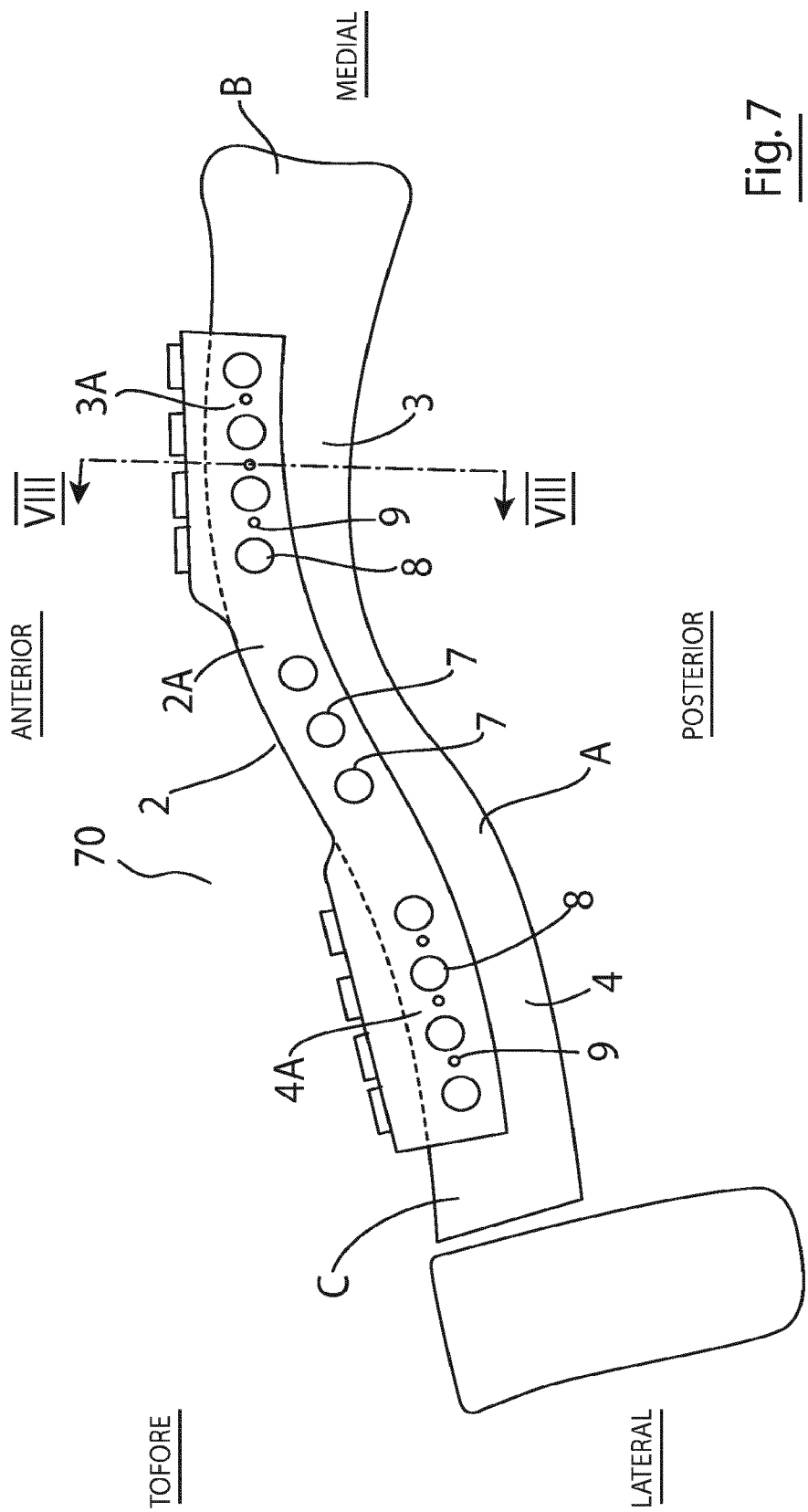
FIG. 7 is an inferior view of a bone reduction and fixation plate according to an alternative embodiment of the invention configured for anterior-inferior reduction and fixation, shown attached to a right human clavicle (inferior view).
Figure 8:
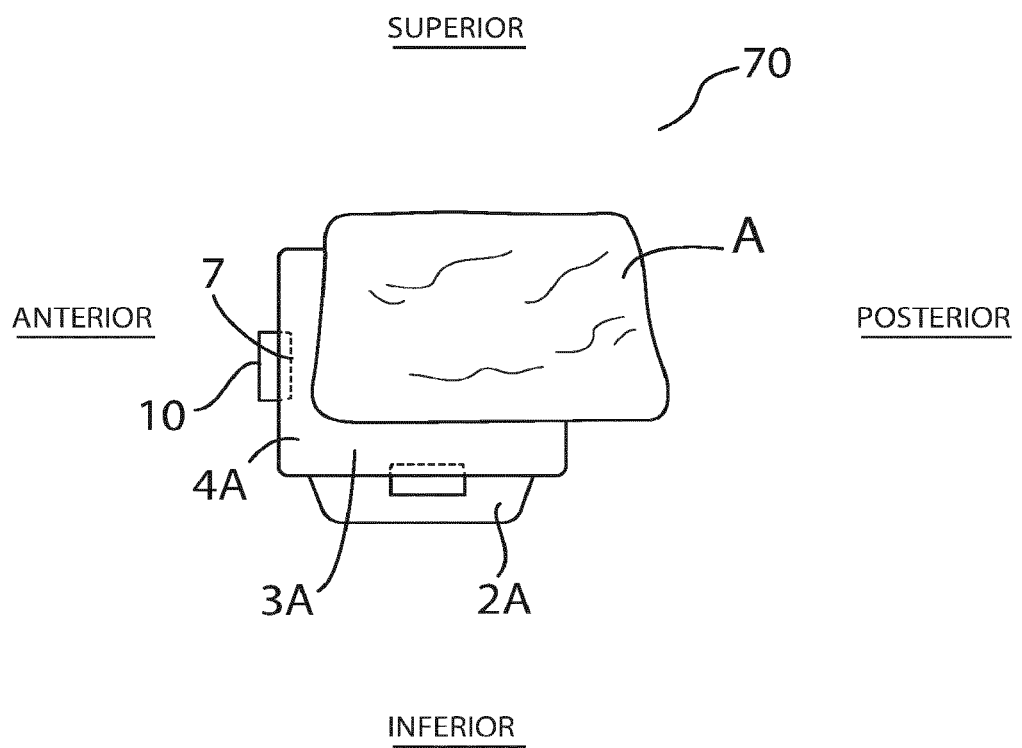
FIG. 8 is a sectional, or sagittal view taken along the lines VIII-VIII of FIG. 7.

Referring to FIGS. 7 to 10 an alternative embodiment of the invention is described, indicated generally by the reference numeral 70, in which parts described with reference to the previous embodiment are assigned the same reference numerals. In the previous embodiments described with reference to FIGS. 1 to 6, the plate is configured to align with the clavicle in a superior-anterior orientation. In the embodiment of FIGS. 7 to 10, the plate is designed and contoured to align with a clavicle in an inferior-anterior orientation which is best illustrated in FIG. 7 which is a view from underneath the clavicle, or in FIGS. 9 and 10 which are anterior views of the plate attached to the clavicle. In this embodiment, the plate has a slight pre-contoured curve along the anterior face which matches the sigmoid curve on the anterior surface of the clavicle A.

Figure 9:
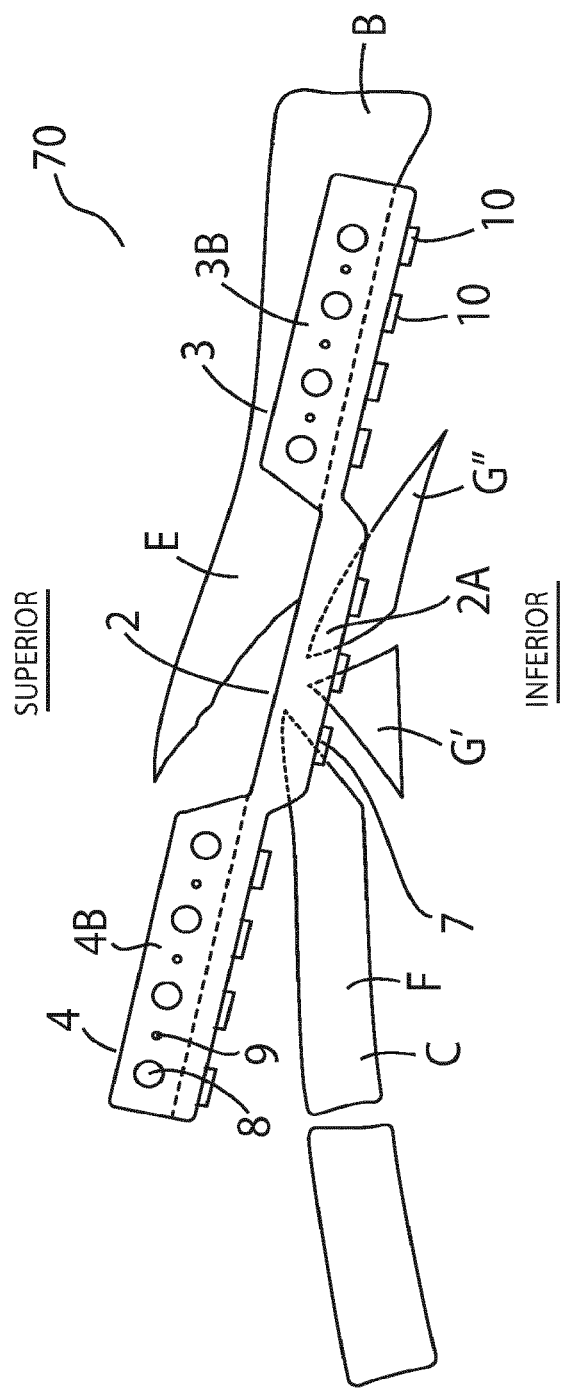
FIG. 9 is an anterior view of the plate of FIG. 7 in use in reducing and fixing a comminuted fracture of a clavicle, showing one L-shaped end portion of the device (medial end portion) attached to a medial clavicle fragment and prior to the attachment of the device to the lateral fragment.
Figure 10:
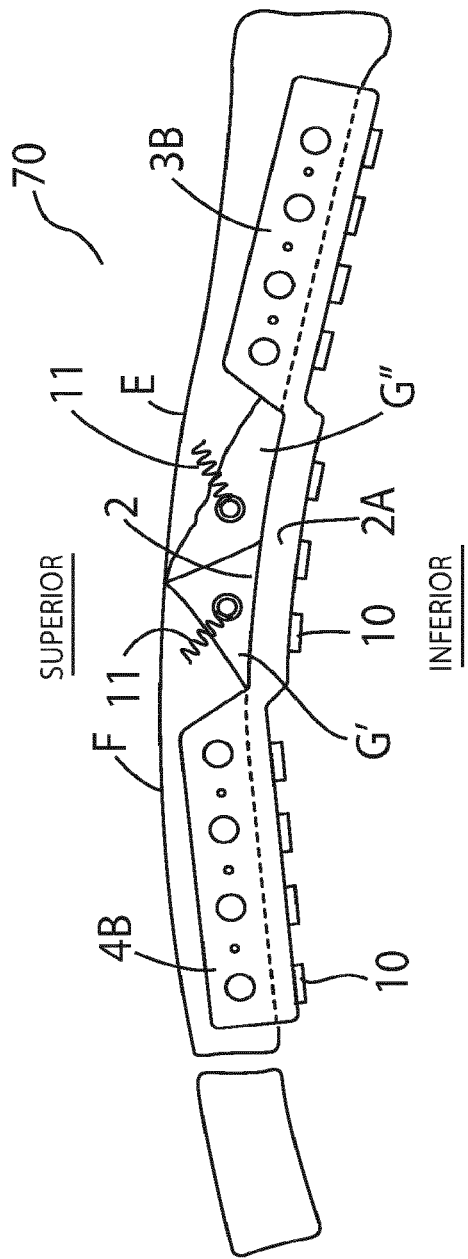
FIG. 10 shows the other L-shaped end portion of the device (lateral end portion) attached to the lateral fragment and the bone reduced and fixed. It also illustrates how the lag window (monoplanar window section) provides access for the surgeon during reduction and fixing to the smaller bone fragments allowing them to be reduced and fixed in position.

In use, and referring to FIGS. 9 and 10, the medial fragment E is aligned with the medial end 3 of the plate, with the bone nestling in the L-shaped profile as shown in FIG. 9. Once in position, the bone is fixed to the plate by drilling a hole in the bone through a countersunk hole 8, and inserting a screw into the hole and tightening to fix the medial end of the plate to the medial fragment. The lateral fragment F can then be manipulated to align it with the lateral end 4 of the plate, with the bone nestling in the L-shaped profile of the plate. Once aligned, the lateral position of the fragment F and plate 1 can then be easily adjusted until the fragments of bone reduce together. Additional lag screws 11 have been employed to fix the comminuted fragment G' to the end of the lateral fragment F and the comminuted fragment G" to the end of the medial fragment E. As the bone fragments both nestle within co-aligned L or C-shaped plates, the only adjustment necessary is lateral adjustment to bring the bones together to reduce. Once they are in position, the lateral fragment F can be fixed to the lateral end section 4 of the plate. At this point, or prior to fixing the lateral fragment of the plate, the position of the medial fragment E with respect to the plate can be fine adjusted by loosening the screw in the countersunk hole 8 and slightly adjusting the position of the medial fragment E and plate 1.

Figure 11:
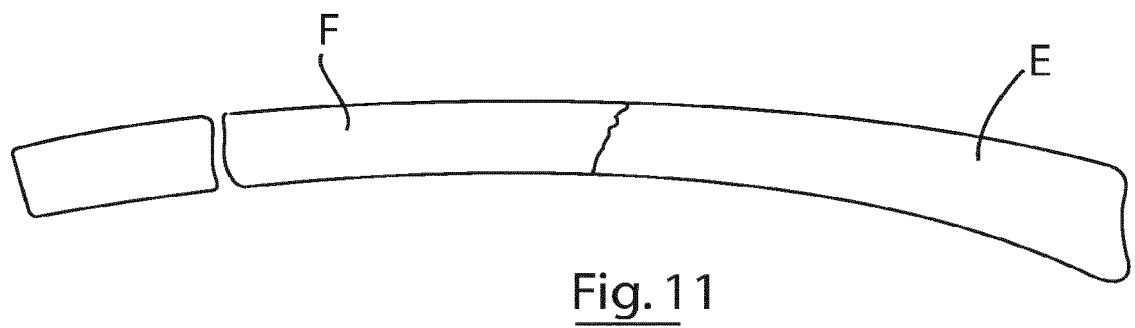
FIG. 11 is an illustration of a 2-part undisplaced clavicular fracture showing the medial and lateral main bone fragments.
Figure 12:
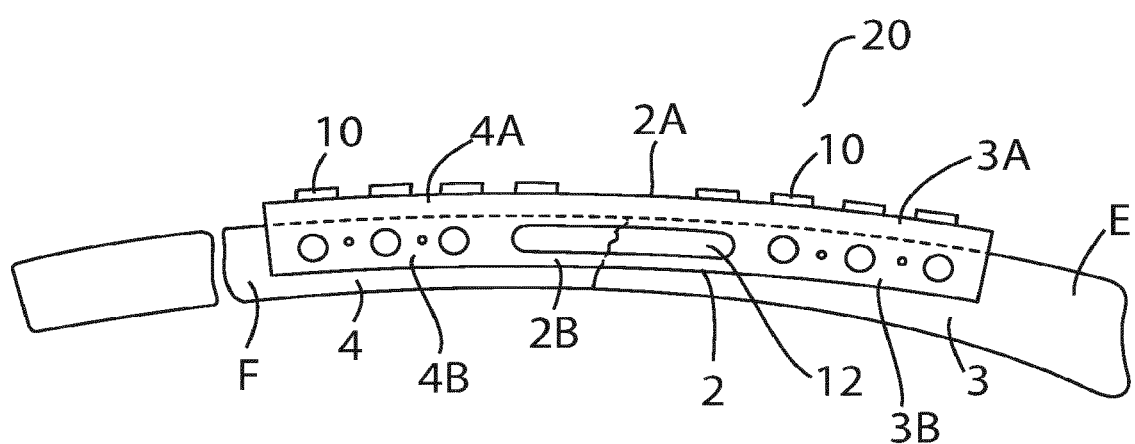
FIG. 12 is an illustration of the plate of the invention attached to the fractured clavicle of FIG. 11, showing how the elongated slot in the central side plate allows the surgeon access to the bone reduction point, in order to assess for anatomical reduction.

FIG. 11 shows an undisplaced fractured clavicle with a break, or fracture in the midshaft. FIG. 12 shows an alternative embodiment of the bone reduction and fixation plate of the invention attached to the fractured clavicle of FIG. 11, indicated generally by the reference numeral 20, in which parts identified with reference to the previous embodiment are assigned the same reference numerals. In this embodiment, the device is biplanar along its length, and a central part 2B of the second (anterior) plate has an elongated slot 12 that allows surgical access to the ends of the bone fragments and allow vascularisation of the healing bone. The central part of the first plate 2A has the same thickness (about 2 mm) as the ends of the first plate, and second plate. The use of this embodiment is substantially the same as that described with reference to FIGS. 1 to 4. Although not illustrated, the central part of the first plate 2A may have a greater thickness than the end sections of the first plate 2A.

Figure 13:
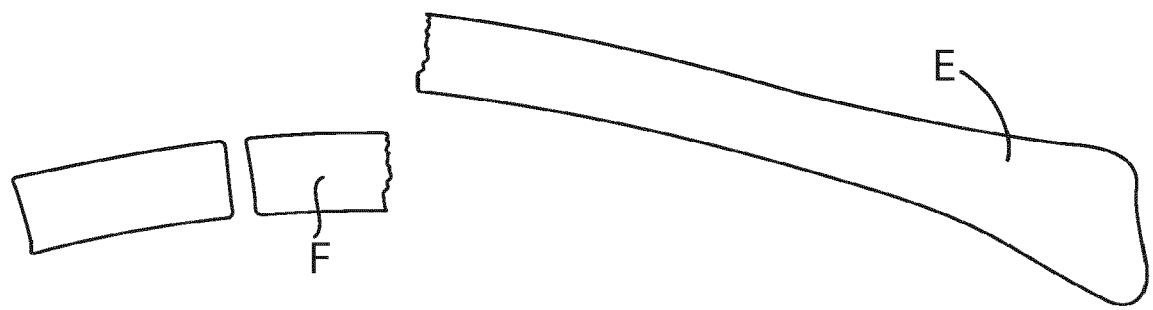
FIG. 13 is an illustration of the typical appearance of a fracture of the lateral end of the clavicle, showing the medial and lateral main bone fragments.
Figure 14:
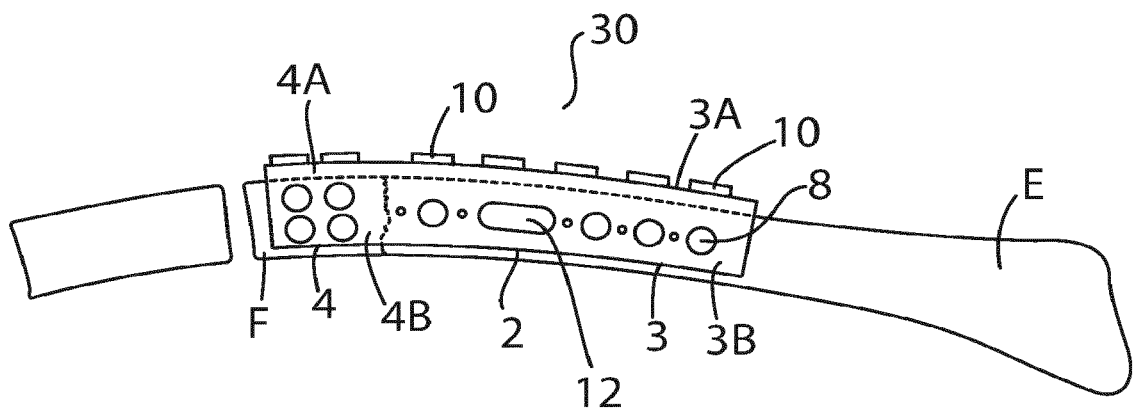
FIG. 14 is an illustration of the plate of the invention attached to the fractured clavicle of FIG. 13 (anterior view). In contrast to the plate for midshaft fractures, there are 4 holes anteriorly, and a further 4 superiorly at the distal, or acromial end of the plate, which allows for greater biomechanical load to failure, and the holes can be filled based on surgeon preference.
Figure 15:
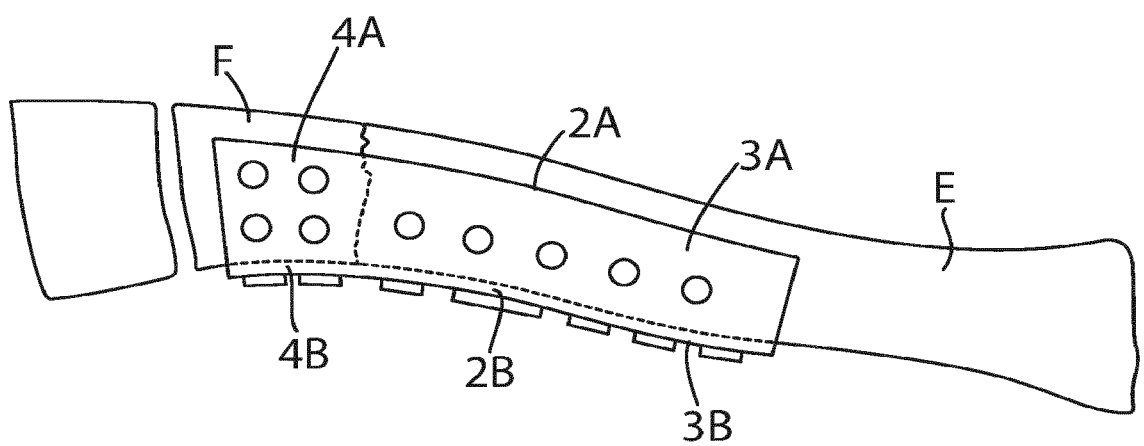
FIG. 15 is an illustration of the lateral plate of the invention attached to the fractured clavicle of FIG. 9 (superior view).

FIG. 13 shows a lateral fracture of the clavicle. FIG. 14 shows an alternative embodiment of the bone reduction and fixation plate of the invention attached to the fractured clavicle of FIG. 13, indicated generally by the reference numeral 30, in which parts identified with reference to the previous embodiment are assigned the same reference numerals. In this embodiment, the device is biplanar along its length, and a central part 2B of the second (anterior) plate has an elongated slot 12 on the which allows surgical access to the ends of the bone fragments and allow vascularisation of the healing bone. The central part of the first plate 2A has the same thickness (about 2 mm) as the ends of the first and second plates. The use of this embodiment is substantially the same as that described with reference to FIGS. 1 to 4.

The embodiments of FIGS. 1 to 15 are especially suited to reduction and fixation of clavicles. The following embodiments exemplify devices according to the invention suitable for reduction and fixation of other bones, such as the ankle (FIGS. 16 and 17) and elbow (FIGS. 18-21).

Figure 16:
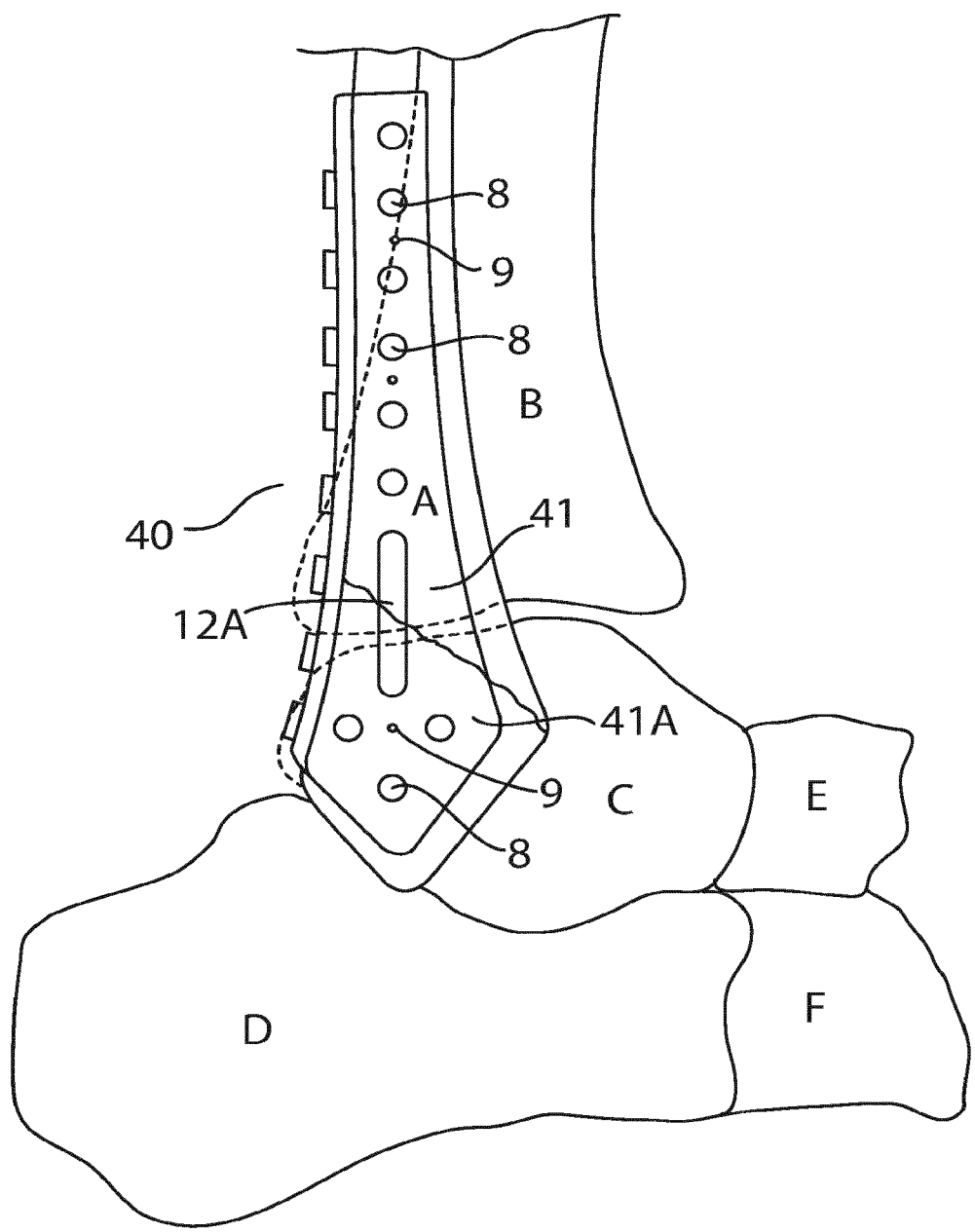
FIG. 16 and FIG. 17 are illustrations of a device according to the invention for reduction and fixation of an ankle (fibula) fracture.
Figure 17:
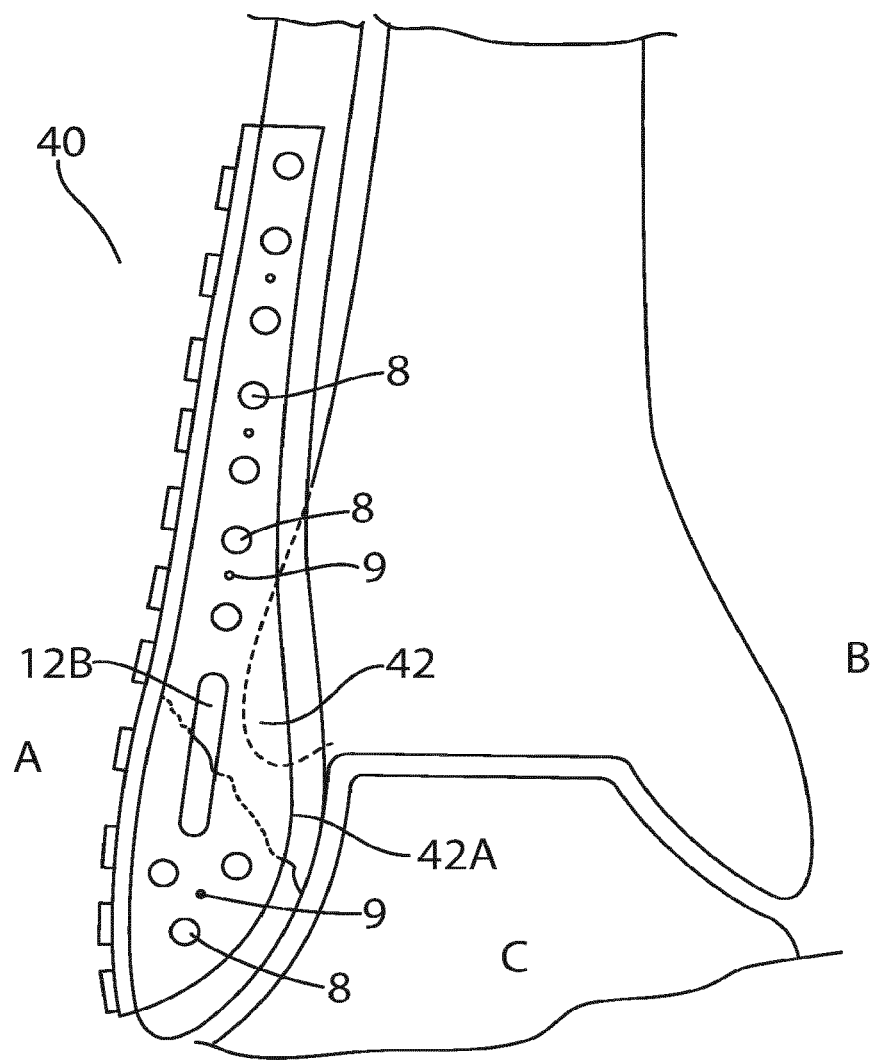

FIGS. 16 and 17 show an embodiment of the bone reduction and fixation plate of the invention for fixing the fibula, indicated generally by the reference numeral 40, in which parts identified with reference to the previous embodiment are assigned the same reference numerals. In this embodiment, the device 40 is a biplanar plate having an L-shaped profile along its full length, and comprising a first (lateral) plate 41 and second (posterior) plate 42. The plate is shown attached to an end of a fractured fibula A, and the other bones of the ankle, namely the tibia B, talus C, calcaneus D, navicular E and cuboid F are illustrated. A distal end 41A of the lateral plate 41 is widened (FIG. 16) to approximately conform to a lateral surface of the fibula A, and includes an elongated slot 12A that in use overlies the fracture allowing access to it. Likewise, a distal end 42A of the posterior plate 42 is widened (FIG. 17) to approximately conform to a posterior surface of the fibula A, and also includes an elongated slot 12B that in use also overlies the fracture allowing access to it, but also allowing the use of an interfragmentary lag screw. The end of the plates distal of the slots comprises three countersunk holes 8 and one wire-receiving hole 9, and the end of the plates proximal of the slots comprises six countersunk holes 8 and three wire-receiving hole 9. The use of this embodiment is substantially the same as that described with reference to FIGS. 1 to 4.

Figure 18:
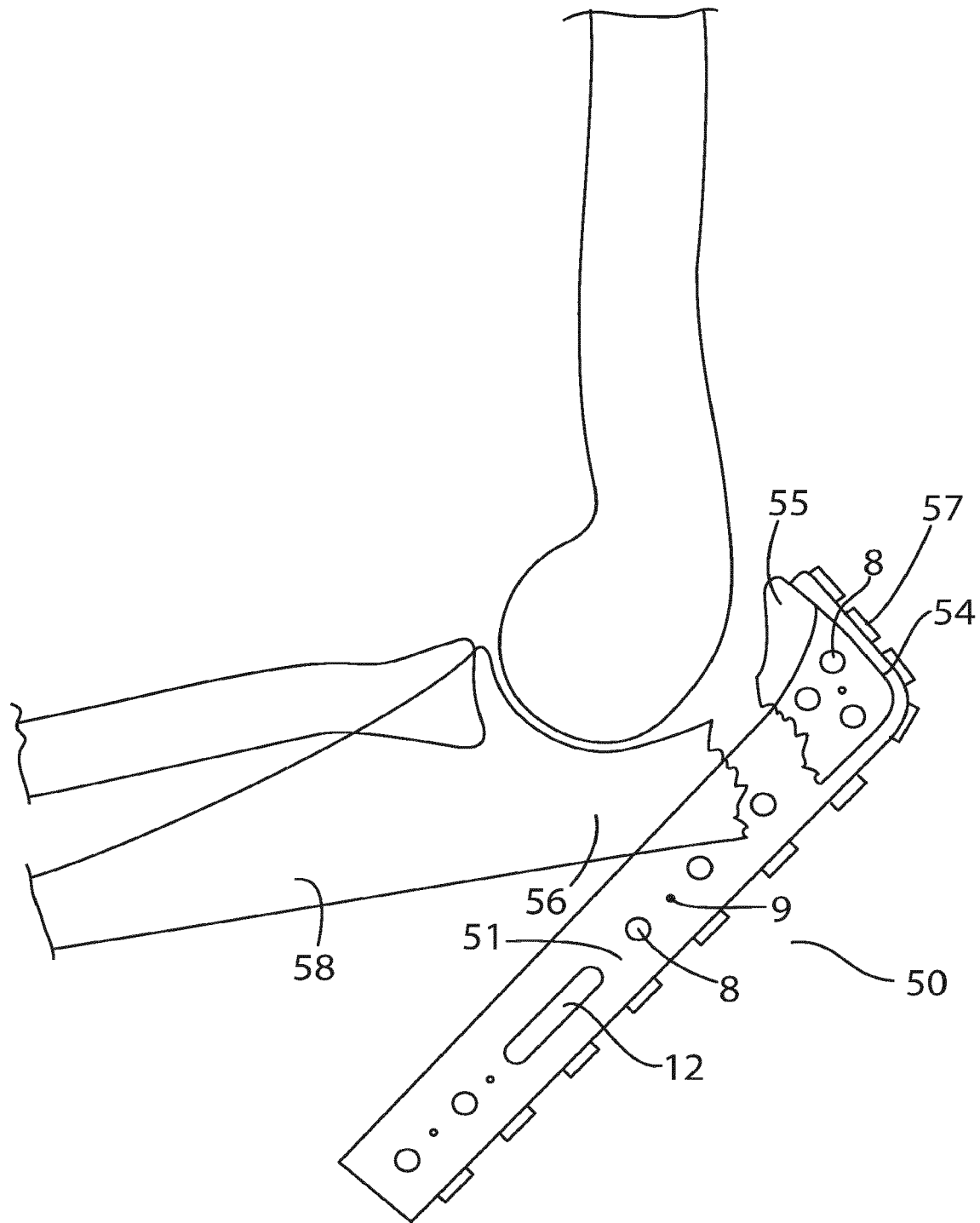
FIGS. 18-20 are illustrations of a device according to the invention for reduction and fixation of an olecranon (elbow) fracture.
Figure 19:
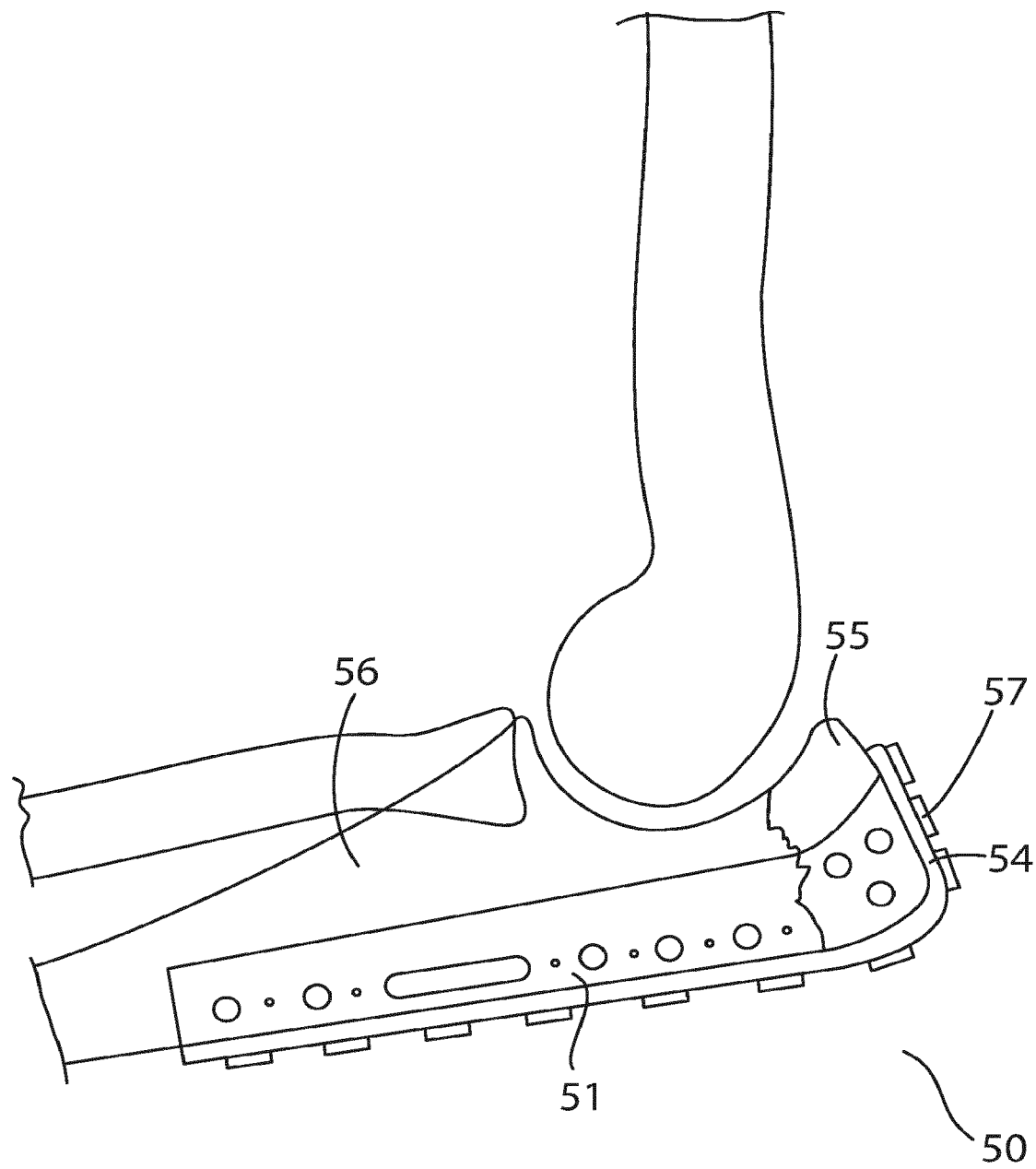
Figure 20:
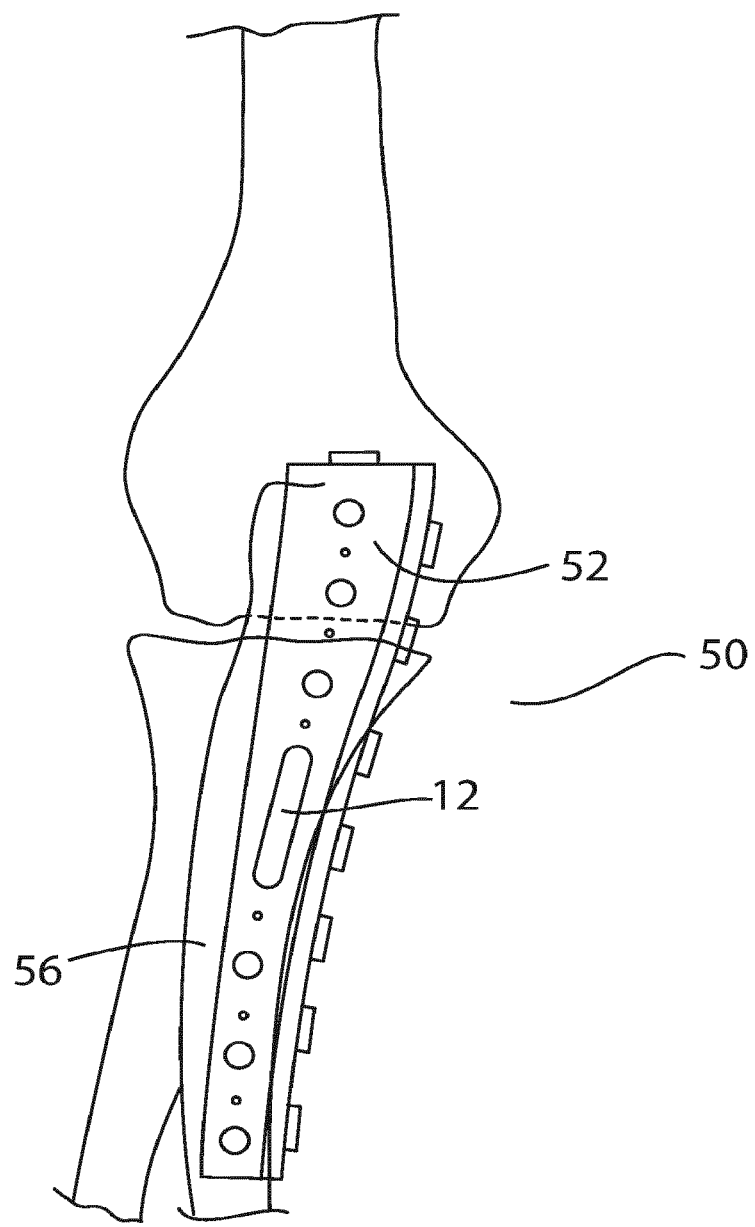

FIGS. 18 to 20 show an embodiment of the bone reduction and fixation plate of the invention for fixing an olecranon (ulna bone), indicated generally by the reference numeral 50, in which parts identified with reference to the previous embodiment are assigned the same reference numerals. In this embodiment, the device 50 is a biplanar plate having an L-shaped profile along its full length, and comprising a first (lateral) plate 51 and second (anterior) plate 52. Both plates include a plurality of screw-receiving holes 8 and smaller wire holes 9, and an elongated slot 12. A proximal hooked end of the biplanar plate 53 comprises an end plate 54, and the anterior plate 52 and end plate 54 are contoured to conform to the end of the ulna (as shown in FIG. 18). In FIG. 18, the plate is shown at the start of a reduction part of the procedure, attached to a first end 55 of a fractured ulna 58, by wires (not shown). FIG. 19 shows the next stage of reduction in which the second end of the fractured ulna 56 is reduced to the first end using the L-shaped profile of the device as a guide. Once the bones have been reduced as shown in FIG. 19, bone-fixing screws 10 are put in place, including a long intermedullary screw 57. The use of this embodiment is substantially the same as that described with reference to FIGS. 1 to 4.

Figure 21:
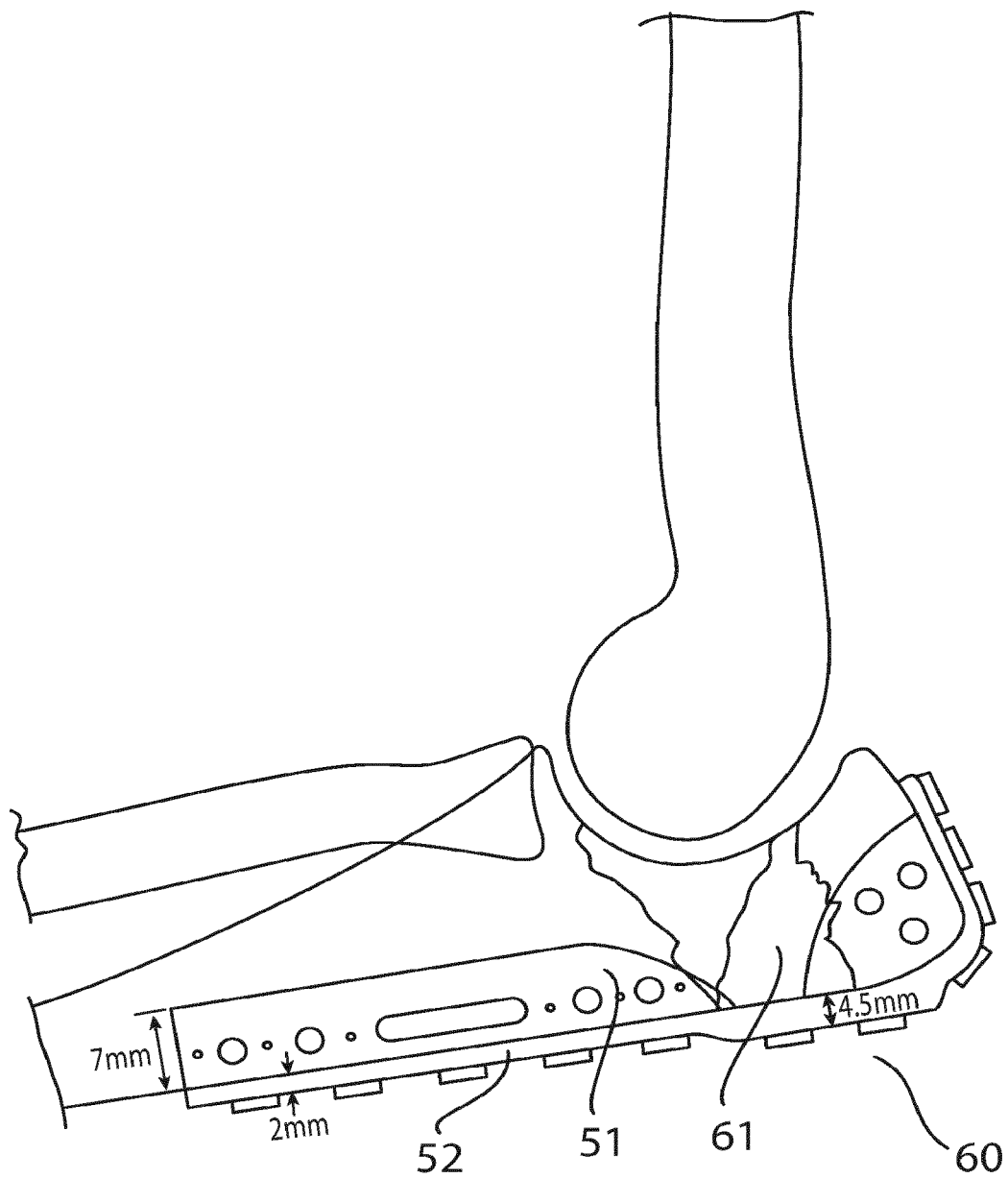
FIG. 21 is an illustration of another device according to the invention for reduction.

FIG. 21 shows another embodiment of the bone reduction and fixation plate of the invention for fixing an olecranon (ulna bone), indicated generally by the reference numeral 60, in which parts identified with reference to the previous embodiment are assigned the same reference numerals. In this embodiment, the device 60 is substantially identical to the device described with reference to FIGS. 18-20, with the exception that the device includes a lag window 61 to allow access to reduce and fix comminuted bone fragments. The use of this embodiment is substantially the same as that described with reference to FIGS. 5 and 6.

The plates of the invention, by virtue of their L shaped profile which extends along one or both ends of the plate, and in some cases, along the full length of the plate, allow for easier alignment of bone fragments with the plate, providing easier and more accurate bone reduction and fixation, while also providing a plate with better bending and torsional stiffness and having a lower profile. The embodiment with a L shaped profile at the end sections only, provides an access window to the central, anterior surface of the bone, allowing access to comminuted bone fragments and inhibiting devascularisation of the healing bone fragments. The loss of bending and torsional stiffness due to the lack of an L shaped profile in the central section is compensated for by increasing the thickness of the plate at the central section. Examples of L-shaped profiles applicable to the biplanar plates of the present invention are provided in FIG. 22.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

The invention claimed is:

1. A bone reduction and fixation device comprising:
   a central section;
   a medial end section; and
   a lateral end section,
   the medial end section and the lateral end section each having an L-shaped profile defined by ends of a first (superior) plate and two second (anterior) plates,
   the central section comprising a central part of the first plate and no second plate, thus providing a lag window,
   wherein the lag window is positioned to enable access to reduce and fix comminuted bone fragments,
   wherein the L-shaped profile results when the first (superior) plate is orthogonal or nearly orthogonal to the second (anterior) plate along at least a part of its length,
   wherein a central section of the first plate has two countersunk screw-receiving holes, and end sections of each plate have three countersunk screw receiving holes.

2. The bone reduction and fixation device of claim 1 further comprising smaller wire-receiving holes on the plates in-between the screw-receiving holes.

3. An elongated biplanar plate comprising:
two biplanar L-shaped end sections and a monoplanar central section defined by a continuous first plate and two end second plates, in which the first plate at the monoplanar central section has a thickness at least 30% greater than the thickness of the first plate at the L-shaped end sections,
wherein each second plate comprises at least two holes.

4. A clavicle reduction and fixation device comprising:
an elongated monoblock biplanar plate having an L-shaped profile along most of its length defined by a first plate; and
one or more second plates,
wherein the first and second plates each comprise one or more holes configured for receipt of bone-fixing screws,
wherein the biplanar plate comprises two biplanar L-shaped end sections and a monoplanar central section and is defined by a continuous first plate and two end second plates,
wherein in the first plate of the monoplanar central section has a thickness at least 30% greater than the thickness of the first plate at the L-shaped end sections,
wherein the first plate and second plates at the L-shaped end sections have a thickness of 1.5 to 2.5 mm,
wherein the first plate at the monoplanar central section has a thickness of 4 to 6 mm.

5. A bone reduction and fixation device comprising:
a central section;
a medial end section; and
a lateral end section,
the medial end section and the lateral end section each having an L-shaped profile defined by ends of a first (superior) plate and two second (anterior) plates,
two or more countersunk screw-receiving holes for both the first (superior) plate and the medial end section,
the central section comprising a central part of the first plate and no second plate, thus providing a lag window,
the lag window positioned to enable access to reduce and fix comminuted bone fragments, the L-shaped profile resulting when the first (superior) plate is orthogonal or nearly orthogonal to the second (anterior) plate along at least a part of its length,
a central section of the first plate having at least one more countersunk screw-receiving holes, and end sections of each plate having at least one or more countersunk screw receiving holes.

6. A bone reduction and fixation device comprising:
a central section;
a medial end section; and
a lateral end section,
the medial end section and the lateral end section each having an L-shaped profile defined by ends of a first (superior) plate and two second (anterior) plates,
the central section comprising a central part of the first plate and no second plate, thus providing a lag window,
the lag window positioned to enable access to reduce and fix comminuted bone fragments,
the L-shaped profile resulting when the first (superior) plate is orthogonal or nearly orthogonal to the second (anterior) plate along at least a part of its length,
a central section of the first plate having at least one more countersunk screw-receiving holes, and end sections of each plate having at least one or more countersunk screw receiving holes,
at least one countersunk screw receiving holes in central section of first plate, and
end sections of each plate having two or more countersunk screw receiving holes.

7. A bone reduction and fixation device comprising:
a central section;
a medial end section; and
a lateral end section,
the medial end section and the lateral end section each having an L-shaped profile defined by ends of a first (superior) plate and two second (anterior) plates,
the central section comprising a central part of the first plate and no second plate, thus providing a lag window,
the lag window positioned to enable access to reduce and fix comminuted bone fragments,
the L-shaped profile resulting when the first (superior) plate is orthogonal or nearly orthogonal to the second (anterior) plate along at least a part of its length,
a central section of the first plate having at least one more countersunk screw-receiving holes, and end sections of each plate having at least one or more countersunk screw receiving holes,
at least one countersunk screw receiving holes in central section of first plate,
end sections of each plate having two or more countersunk screw receiving holes,
wherein a central section of the first plate has two countersunk screw-receiving holes, and end sections of each plate have three countersunk screw receiving holes.

8. A clavicle reduction and fixation device comprising:
an elongated monoblock biplanar plate having an L-shaped profile along most of its length defined by a first plate; and
one or more second plates,
wherein the first and second plates each comprise one or more holes configured for receipt of bone-fixing screws,
wherein the biplanar plate comprises two biplanar L-shaped end sections and a monoplanar central section and is defined by a continuous first plate and two end second plates,
wherein in the first plate of the monoplanar central section has a thickness at least 30% greater than the thickness of the first plate at the L-shaped end sections,
wherein the first plate and second plates at the L-shaped end sections have a thickness of at least 1.5 to 2.5 mm,
wherein the first plate at the monoplanar central section has a thickness of 2 to 6 mm.

9. A clavicle reduction and fixation device comprising:
an elongated monoblock biplanar plate having an L-Shaped profile along most of its length defined by a first plate; and
one or more second plates,
wherein the first and second plates each comprise one or more holes configured for receipt of bone-fixing screws,
wherein the biplanar plate comprises two biplanar L-shaped end sections and a monoplanar central section and is defined by a continuous first plate and two end second plates,
wherein in the first plate of the monoplanar central section has a thickness at least 30% greater than the thickness of the first plate at the L-shaped end sections, wherein the first plate and second plates at the L-shaped end sections have a thickness of at least 1.5 to 2.5 mm, wherein the first plate at the monoplanar central section has a thickness of 4 to 6 mm.

10. A clavicle reduction and fixation device comprising:

an elongated monoblock biplanar plate having an L-shaped profile along most of its length defined by a first plate; and one or more second plates, wherein the first and second plates each comprise one or more holes configured for receipt of bone-fixing screws, wherein the biplanar plate comprises two biplanar L-shaped end sections and a monoplanar central section and is defined by a continuous first plate and two end second plates, wherein in the first plate of the monoplanar central section has a thickness at least 30% greater than the thickness of the first plate at the L-shaped end sections, wherein the first plate and second plates at the L-shaped end sections have a thickness of at least 1.5 to 3.7 mm, wherein the first plate at the monoplanar central section has a thickness of 4 to 6 mm.

\* \* \* \* \*